(12) United States Patent
Tsou

(10) Patent No.: US 6,851,430 B2
(45) Date of Patent: Feb. 8, 2005

(54) METHOD AND APPARATUS FOR ENDOSCOPIC SPINAL SURGERY

(76) Inventor: Paul M. Tsou, 2001 Santa Monica Blvd., Suite 1190 W., Santa Monica, CA (US) 90404

(\*) Notice: Subject to any disclaimer, the term of this patent is extended or adjusted under 35 U.S.C. 154(b) by 0 days.

(21) Appl. No.: 09/997,361

(22) Filed: Nov. 30, 2001

(65) Prior Publication Data

US 2002/0077632 A1 Jun. 20, 2002

Related U.S. Application Data

(60) Provisional application No. 60/333,038, filed on Nov. 16, 2001.

(51) Int. Cl.[7] .......................... A61B 19/00; A61B 17/32
(52) U.S. Cl. ............................ 128/898; 606/79; 606/86
(58) Field of Search ............................. 606/79; 128/898

(56) References Cited

U.S. PATENT DOCUMENTS

| | | |
|---|---|---|
| 4,545,374 A | 10/1985 | Jacobson |
| 5,501,654 A | 3/1996 | Failla et al. |
| 5,792,044 A | 8/1998 | Foley et al. |
| 5,902,231 A | 5/1999 | Foley et al. |
| 6,217,509 B1 | 4/2001 | Foley et al. |
| 6,261,311 B1 | 7/2001 | Sharkey et al. |
| 6,270,498 B1 | 8/2001 | Michelson |

OTHER PUBLICATIONS

[Author not identified], "Posterior 4022 Paddle Tube Surgical Technique BAK Lumbaar Interbody Fusion System;" Brochure Copyright 1999, 23 pages, published by Sulzer Medica, Minneapolis, MN 55439–2027, U. S. A.

Primary Examiner—Cary E. O'Connor
Assistant Examiner—Candice C. Stokes
(74) Attorney, Agent, or Firm—Kleinberg & Lerner, LLP

(57) ABSTRACT

A method of performing percutaneous transforaminal endoscopic lumbar surgery on a patient, includes the steps of creating an opening in the patient's skin, passing at least one tubular cannula through the opening so as to create a soft tissue tunnel, placing a semi-tubular spreader over the at least one tubular cannula inside the soft tissue tunnel, placing a flat blade spreader into an opening formed by the semi-tubular spreader, dilating the opening by spreading apart blades of the flat blade spreader, inserting bone grafts through the opening and into an intervertebral space of the patient.

16 Claims, 11 Drawing Sheets

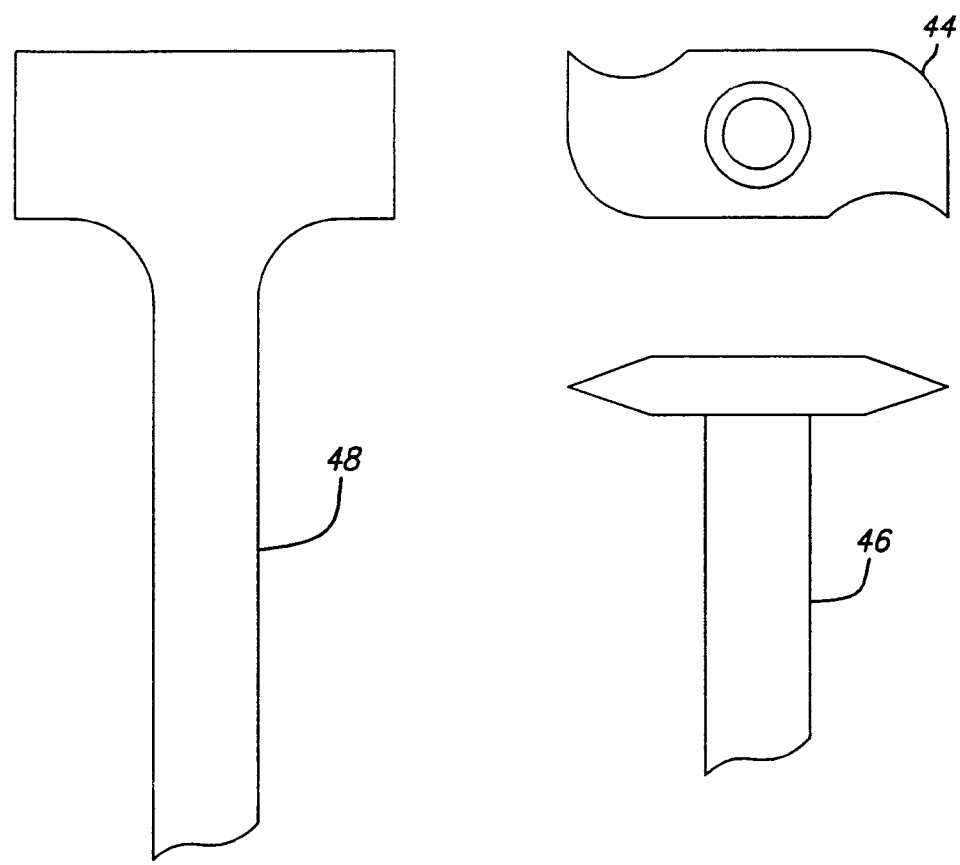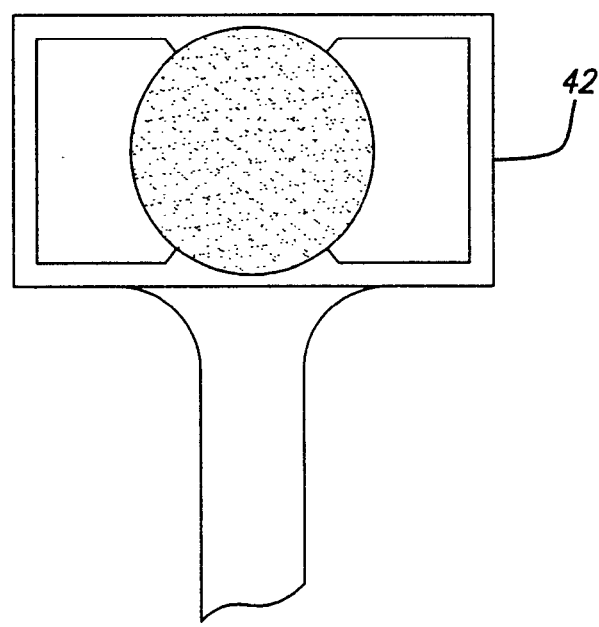
FIG. 8

METHOD AND APPARATUS FOR ENDOSCOPIC SPINAL SURGERY

The present application is a continuation-in-part of U.S. provisional patent application Ser. No. 60/333,038 filed Nov. 16, 2001.

BACKGROUND OF THE INVENTION

1. Field of the Invention

The present invention relates generally to methods and apparatus for percutaneous surgery and, more specifically, to a method and apparatus for performing percutaneous transforaminal lumbar and thoracic disc surgery and interbody fusion.

2. Description of Prior Art

A substantial segment of the population suffers from spinal pain that is caused by degenerative, herniated or protruded intervertebral discs. Intervertebral discs are members of the spinal column that serve as cushions and mobile linkage elements between the individual vertebrae. The acute herniation of an intervertebral disc can lead to the compression of spinal nerve elements within the spinal canal as well as disc surfaces outside of the spinal canal. The problem can cause severe back pain, leg pain, muscle weakness, and possibly bowel and bladder dysfunction.

The traditional surgical method of spinal nerve element decompression is by the transcanal methods of laminectomy or laminotomy. Optical aids such as microscopes, endoscopes or loupes are often used in these processes. The tissue retractor commonly used in this type of surgery is normally constructed with two blades. More recently, a tubular shaped retractor has been used. Traditionally, this procedure has required two to three days of hospitalization after completion of the surgery.

Chronic back pain due to disc failure, without dominant extremity symptoms may also cause chronic functional impairment. Prior art solutions have surgically fused adjacent vertebrae together by placing bridging bone material from one vertebra above to one vertebrae below the symptomatic disc(s). The bone fusion surfaces may include the posterior vertebral elements, the vertebral end plates or a combination of the two. Sometimes, metal rods and screws have been used to stabilize the subject spinal fusion segment from the posterior approach.

Because of the tremendously invasive nature of many prior art techniques as compared to the present invention, these prior art techniques caused significant access tissue trauma, even when the skin incision was reduced in length.

Using endoscopic transforaminal techniques, a surgeon can operate through a smaller (roughly 8–12 millimeters) opening with endoscopic surgical viewing instruments and miniaturized tools.

The preferred method using endoscopic techniques and miniaturized instrumentation results in an even less intrusive procedure. Because the access surgical trauma and destabilization are less with this technique, endoscopic transforaminal surgery requires a shorter rehabilitation time.

The preferred technique of the present invention adopts an extraspinal canal approach for the correction of spinal conditions, herniated discs and chronic disc pain. In using this approach, the perils of nerve element and dural from sharp trauma and retraction trauma are greatly reduced. The working channel for simple herniated disc extraction is approximately 8 mm in diameter and the diameter is somewhat larger for fusion surgery. Because of the ultra miniaturization of the instruments, the procedure can be performed using local anesthetic agents and conscious sedation. Unlike prior art, overnight hospital stays are not necessary.

In an alternative methodology, the body is opened up as much as necessary. The remaining portion of the access to the target site is conducted using the minimally invasive techniques and tools as described herein. This surgical technique is less invasive than prior art, but more invasive than the preferred methodology of this invention.

To fuse adjacent vertebrae, bone graft material is placed in the evacuated disc space between the bony end-plate of the target vertebrae. After insertion of the structural bone graft material and any additional non-structural osteogenic agents, ingrowth of new autologous bone gradually replaces the graft material to create a unified structure that includes the first and last vertebrae in the fusion segment. Prior art techniques have used structural angular bone blocks, metallic cages, carbon fiber blocks or bone chips that are inserted into the intervertebral space(s). Prior art laparoscopic anterior lumbar fusion technique uses cylindrical metallic cages or bone dowels. These cylindrical shaped devices do not achieve maximum surface contact with the flat surface of the host end plate bed. Thus, seating of cylindrical/round shaped fillers requires end-plate cutting. Surgical end-plate cutting structurally weakens the end-plate and introduces the probability of metallic fillers settling into the soft vertebral cancellous body. In contrast, the preferred mode of the present invention uses modular discoid shaped fillers that do not need end-plate cutting for seating and stability.

However, prior art lateral approached spinal, square shaped graft delivery tubes are bulky. The dimensions of block graft delivery via a prior art square tube can not take full advantage of the maximum outer dimensions of the delivery tube. Additionally, these prior art systems have no method for graft insertions into the L5-S1 disc space. Because prior art minimally invasive systems require generally round tube delivery conduit, the subsequent graft shape is necessarily round/cylindrical as well.

One specific prior art technique, using a rounded filler, is discussed in U.S. Pat. No. 6,217,509 (the '509 patent). The '509 patent describes an access tubular channel from the skin to the targeted work area (which is only used in the posterior transcanal spinal approaches). The working channel inside the tube allows for the use, as needed, of a viewing element, operating tools, tissue retractors, suction channels and a fluid channel. This method is considered more problematic when used in any other approach. According to the '509 patent, a fluid working environment is not desirable in posterior lumbar surgery. However, a fluid environment is utilized in the present invention without degrading endoscopic vision during the ablation of bone, collagenous tissue or bleeder coagulation. A Holmium-YAG laser, used in a fluid medium, in the present invention, eliminates the problems that encountered by the '509 method.

Additionally, the '509 patent does not identify the necessary skin entry location for instruments insertion nor the safe portal into the vertebral annulus. The present invention describes a skin window localization method, identified the safe foraminal annular window and the trajectory for the instruments. In sequential steps the working cannula, viewing element and all other operating tools enter the same windows. In addition, the deep end of the duty cannula is anchored in the opening of the annular window.

Finally, the '509 method neither describes nor allows for the delivery of modular discoid shaped bone graft material (i.e., components of the module are rectangular or have round edges that face the interior of annulus fibrosus).

Therefore, a surgical method, preferred shaped tool(s) and preferred shaped conduits are needed that allow modular discoid shaped filler components, of variable shape and size, to be implanted into an intervertebral disc space using percutaneous endoscopic transforaminal spinal surgery methodology.

BRIEF SUMMARY OF THE INVENTION

According to the present invention, a method and apparatus are described whereby percutaneous endoscopic transforaminal spinal surgery can use modular discoid shaped components as filler for fusion material, in the intervertebral disc space in the spinal column. In the preferred mode of the invention, the desired final implant composite from the components is discoid in general contour. The individual component(s) have round edges facing the interior of annulus fibrosus and straight edges facing each other. From the frontal view, the components are either half moon or rectangularly shaped.

In the preferred embodiment, the method and apparatus include innovative tools to allow the implantation of the above-mentioned implants into the spinal intervertebral spaces. Also, in the preferred embodiment, the methodology requires the patient to be awake during the procedure. A local anesthetic agent is used to infiltrate the skin window, subcutaneous tissue and trajectory tract with a 6" long, 18-gauge needle and continuing towards the foraminal annular window. The skin window localization is determined by the index disc inclination and the measured length from the center of the disc to the posterior skin surface. The needle insertion trajectory is 25–30 degrees in relationship to the frontal plane in line with the disc inclination. After the foraminal annular window placement of the needle, a thin guide wire is inserted through the needle channel and advanced into the center of the disc.

After the guide wire is accurately positioned, the needle is removed and a cannulated obturator is introduced over the proximate tip of the guide wire and inserted toward the annulus at the foramen. The obturator is then advanced through the annulas at the foraminal location. The tapered tip of the obturator should be positioned within the annulus. The guide wire is then removed and a beveled cannula, which allows greater viewing aperture, is inserted over the obturator. Once the beveled tip of the cannula is well within the annulas, the obturator is removed.

If the methodology is utilized to extract herniated spinal disc material, the herniated nucleus pulposus fragments are excised. An operative endoscope is inserted into the cannula and a working tunnel and cavity are created under the herniated elements. The annular collar is opened using mechanical forceps or a Holmium-YAG laser. The herniated fragment is retrieved through the working space and cannula and the epidural and interdiscal spaces are inspected for completeness of removal of the herniated fragments.

When the spinal pathology requires a fusion procedure, the circular shaped annular fenestration is progressively enlarged by inserting progressively larger diameter fish mouth shaped cannula through the skin. In sequential steps, the last smaller cannula is removed after the next larger cannula is inserted. When the largest anatomically feasible foraminal annular window is dilated with the fish mouthed cannula dilation system, the second largest fish mouthed cannula is kept within the annular opening. The largest and the last inserted cannula is removed and replaced by a same sized semi-tubular fish mouthed spreader. The semi-tubular spreader is next inserted with its blades in the completely closed position. The last fish mouthed cannula in the annular opening is then removed.

With the semi-tubular spreader in place, the annular opening is further dilated. Progressively larger diameter solid rods are placed in the channel portion of the semi-tubular spreader until the opening is dilated to the largest anatomically feasible size.

Once the semi-tubular spreader has achieved maximum dilation, excavation of the nucleus pulposus can be performed. Typically, this includes complete removal of the nucleus pulposus and the vertebral cartilaginous end plates to create a natural discoid shaped cavity for the placement of the preferred modular discoid shaped bone graft components. After the nucleous pulposus has been excavated from the intervertebral disc space, a flat blade spreader is inserted into the channel of the semi-tubular spreader such that it engages the rims of the vertebrae. Both spreaders are rotated, in unison, ninety degrees so that the blades of the flat blade spreader are oriented in a cephalad-caudad direction. After rotating the spreaders, both the flat and the semi-tubular blades remain momentarily intertwined. The flat blade spreader is moderately dilated by inserting progressively thicker rectangular shaped dilator and the spreading actions exerted on the spreader handles. The semi-tubular spreader is then removed.

Additional spreading of the flat blade spreader continues by using thicker rectangular dilators. Ultimately, the rectangular annular opening in height and width should be 8–15 mm.

As has been discussed, the method of the invention is implemented through the use of several tools. Included are covers for the flat blade created tissue tunnel. Several attachment mechanisms, cover to flat blade, are entertained. One is a channel fabricated into the outer surface of the paired flat blades, allowing for the attachment of covers for the open sides of the flat blade spreader. Other attachment mechanisms include clasps and screw-on devises. These fixed attachment methods permit the spreader blades and covers to move as one unit. The rectangular channel, now covered on all four sides, allows smooth passage of maximum sized bone graft without graft entanglement in the soft tissues. Because the entire width of the flat blade spreader is oriented cephalad-caudad inside the disc space, there is no wastage spreader height during the insertion of the bone graft.

A first component of the discoid shaped bone graft is inserted and placed as anteriorly as possible. The first bone graft component is followed by a second. For a small intervertebral space, the second graft component may constitute the final implant. For the larger disc spaces, a rectangular shape modular component can be inserted between the anterior and posteriorly positioned implants. After the structural graft components are in place, the remaining voids of the interspace are filled with non-structural shaped osteoinductive agents.

Further features and advantages of the present invention will be appreciated by reviewing the following drawings and detailed description of the invention.

BRIEF DESCRIPTION OF THE DRAWINGS

FIG. 5a shows the annular floor of the foramen is being removed using forceps.

FIG. 5b shows the foraminal bony roof overhang is being ablated using the Holmium-Yag laser.

FIG. 8 presents tools to excavate the intervertebral disc space.

DETAILED DESCRIPTION OF THE INVENTION

According to the present invention, there is disclosed a method and apparatus for performing percutaneous spinal transforaminal endoscopic interbody fusion using modular discoid shaped graft components.

In the following description, for the purposes of explanation, specific devices, component arrangements and construction details are set forth in order to provide a more thorough understanding of the invention. It will be apparent to those skilled in the art, however, that the present invention may be practiced without these specifically enumerated details and that the preferred embodiment can be modified so as to provide other capabilities, such as the capability for the remote control to operate with other devices. In some instances, well-known structures and methods have not been described in detail so as not to obscure the present invention unnecessarily.

Figure 1:
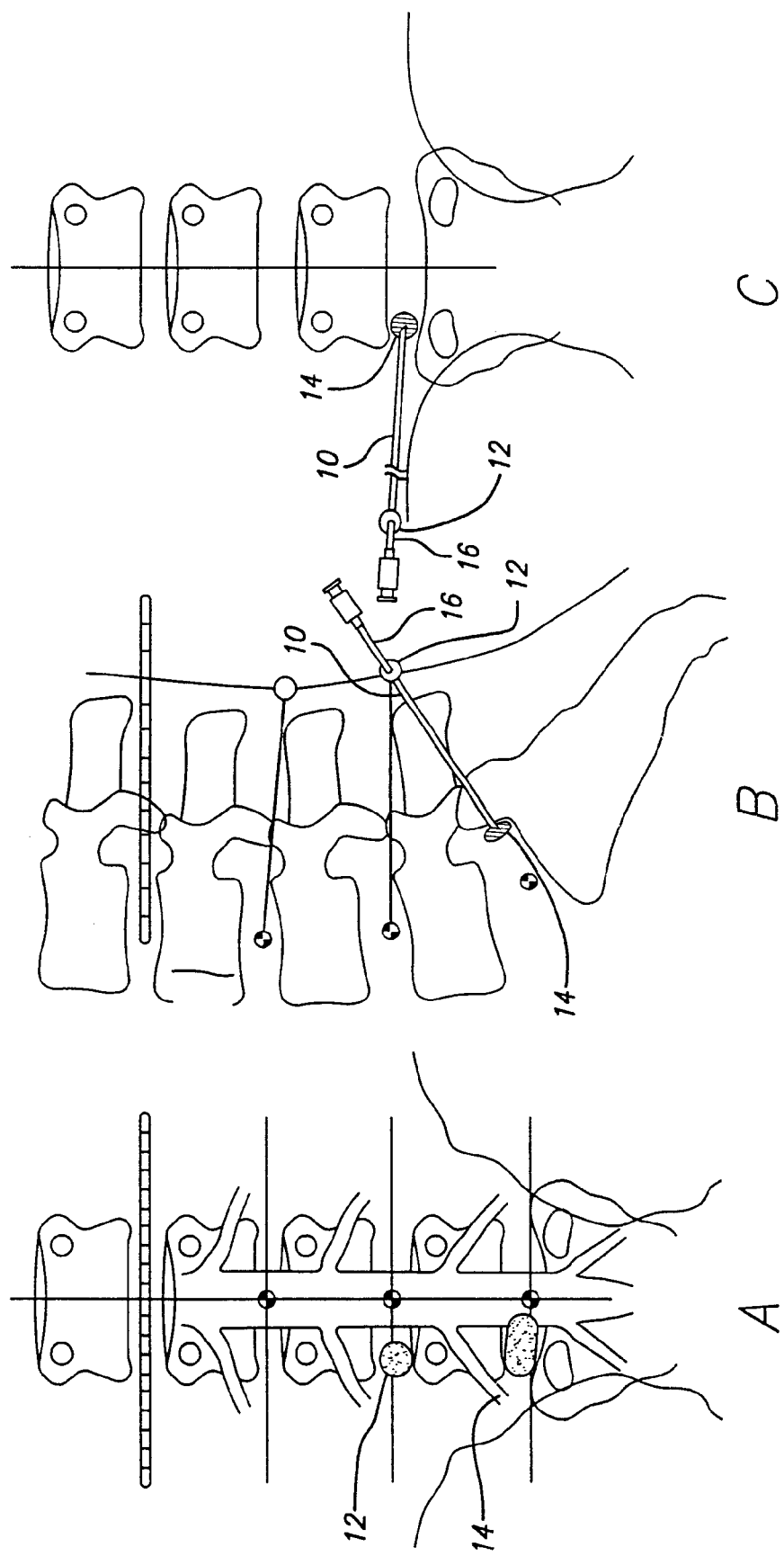
FIG. 1 demonstrates three different C-arm (x-ray) views in the lumbar transforaminal endoscopic approach to the disc.

Referring first to FIG. 1, an approach to percutaneous transforaminal endoscopic lumbar surgery is demonstrated. As seen in A, B and C, the angle of the approach to the disc spaces varies, depending upon the inclination of the targeted intervertebral disc space. The general method of access utilizes a small diameter cannula to create a soft tissue tunnel 10 from an opening in the skin window 12 to the foraminal annular window 14 or a target area.

In the preferred embodiment of percutaneous transforaminal surgery, the target is the foraminal annular window. As shown in FIG. 1, the initial step is to insert a needle following the preferred path from the skin window 12 to the foraminal annular window 14. The preferred embodiment of the present invention utilizes a large bore needle 16. It will be apparent to those of skill in the art that the exact size and diameter of the needle can vary and will depend on the particular treatment needs of the patient.

Figure 2:
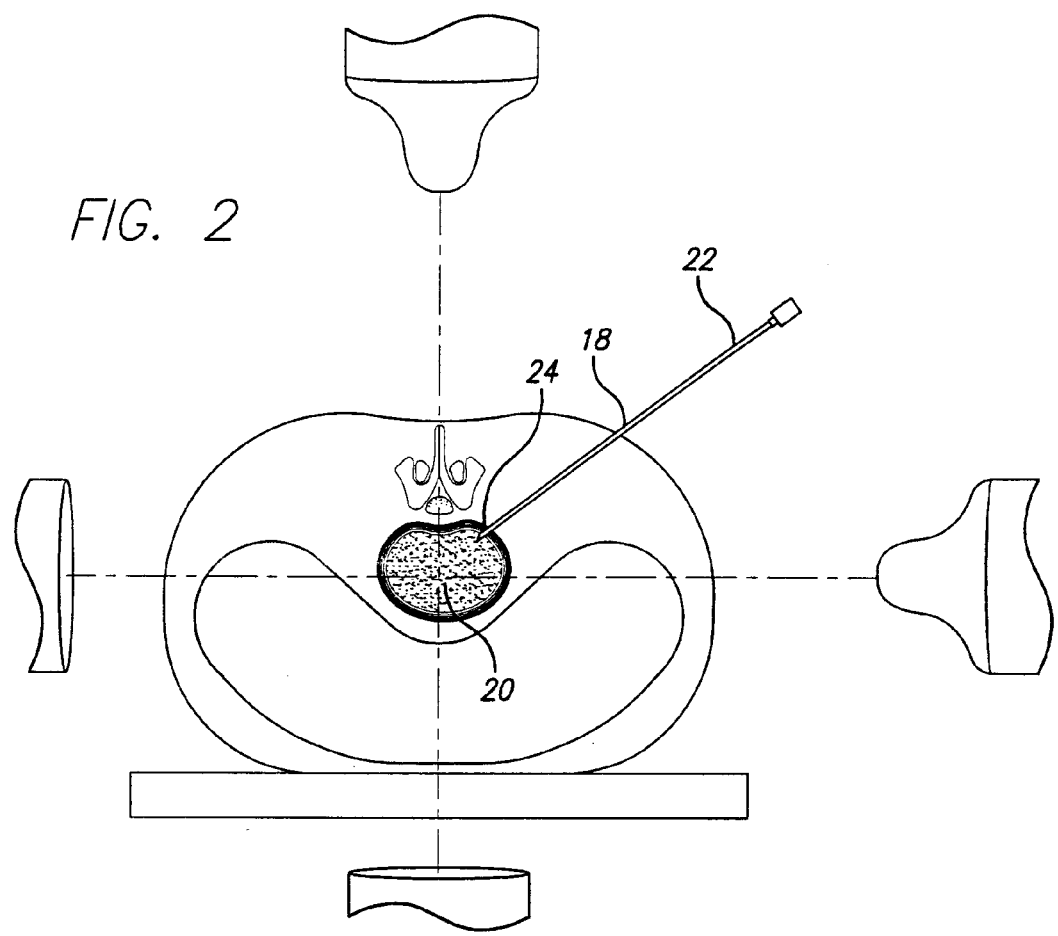
FIG. 2 demonstrates the approach needle trajectory to annular window through a specific skin window determined in the preferred methodology in transforaminal endoscopic lumbar surgery.

Referring next to FIG. 2, in the preferred mode, the invention shows the percutaneous transforaminal endoscopic approach in the axial view. However, the invention can also be used for minimally invasive procedures requiring other modified approaches to the spine. The preferred method of localizing the skin window 18 is to plot the L5-S1 disc inclination in the lateral c-arm projection, as demonstrated by the needle 16 position in FIG. 1. Referring again to FIG. 2, the skin window 18 is determined by measuring distance L from the approximate center of the disc to the posterior skin surface. The distance L is also the distance of skin window from the approximate saggital midline 20 of the patient. The cephalad-caudad location of the skin window is found by the previously plotted disc inclination in the lateral c-arm view.

Initially, a local anesthetic agent is used to infiltrate the skin window 18, subcutaneous tissue and trajectory tract. As noted above, a needle 22 is then inserted from the skin window at approximately 25–30 degrees from the frontal plane anteromedially toward the foraminal annular window. It has been found that in a typical patient, an approximately six inch long, eighteen gauge needle provides satisfactory treatment results. The exact size of the needle 22 may, as noted be smaller or larger, depending on the needs of the individual patient.

Although the preferred embodiment of the method of the present invention utilizes an angle of 25–30 degrees from the frontal plane, it will be apparent to those skilled in the art that a larger or smaller angle can be used in instances where the specific anatomy or treatment needs of the patient require. For example, the patient may have a disk herniation in an unusual location which require access from a different orientation. Alternatively, the patient may have a bone structure which precludes inserting the needle at the preferred angle. In such situations, the surgeon will have sufficient knowledge to determine the most advantageous manner and orientation in which to insert the needle.

Referring again to FIG. 2, the needle 22 is advanced toward the target foraminal annular window 24. In the postero-anterior view, the needle tip is placed approximately in the center of the foraminal annular window 24 between the medial and lateral borders of the pedicle in the foramen and then advanced through the full thickness of the annulus.

A guide wire is then inserted through the needle channel. The guide wire is advanced a sufficient distance to be adjacent to the annulus and the needle is removed. In the preferred embodiment, this distance is approximately one centimeter. A bluntly tapered cannulated obturator 26 (see FIG. 9) is inserted over the guide wire and firmly engages the annulus. The guide wire is then removed.

Figure 4:
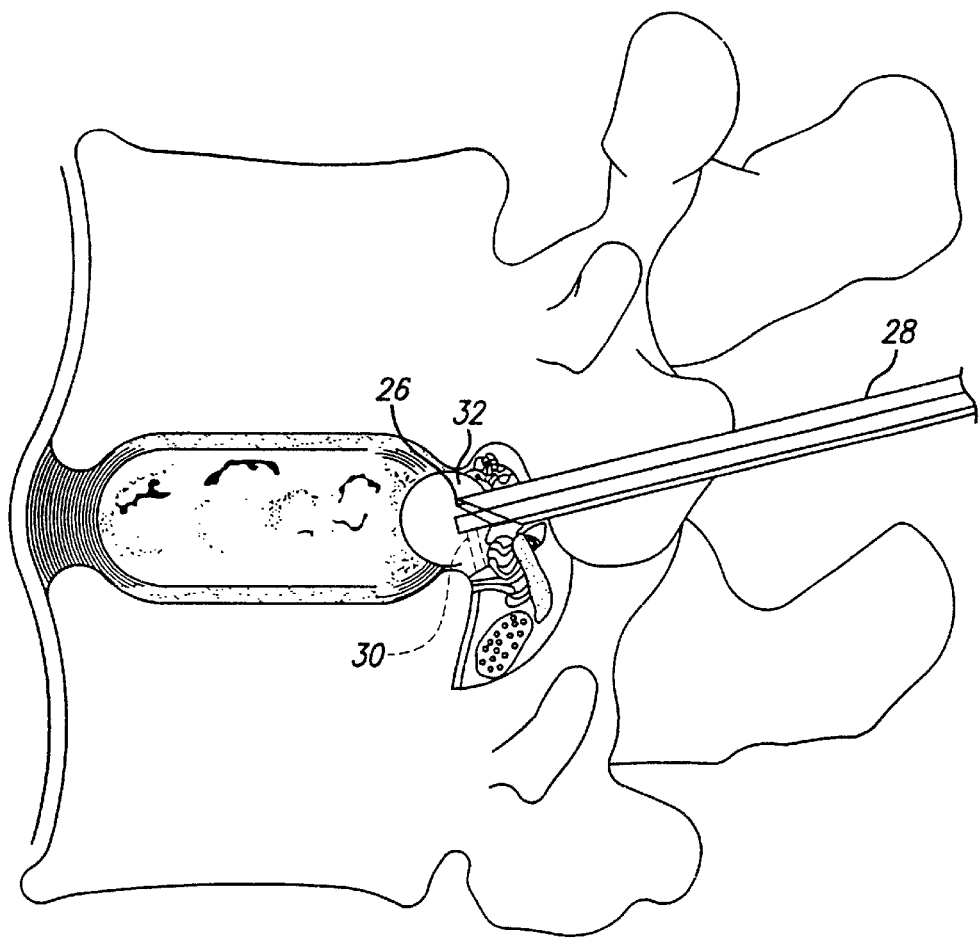
FIG. 4 presents a view of a disc and its adjacent vertebrae.
Figure 5:
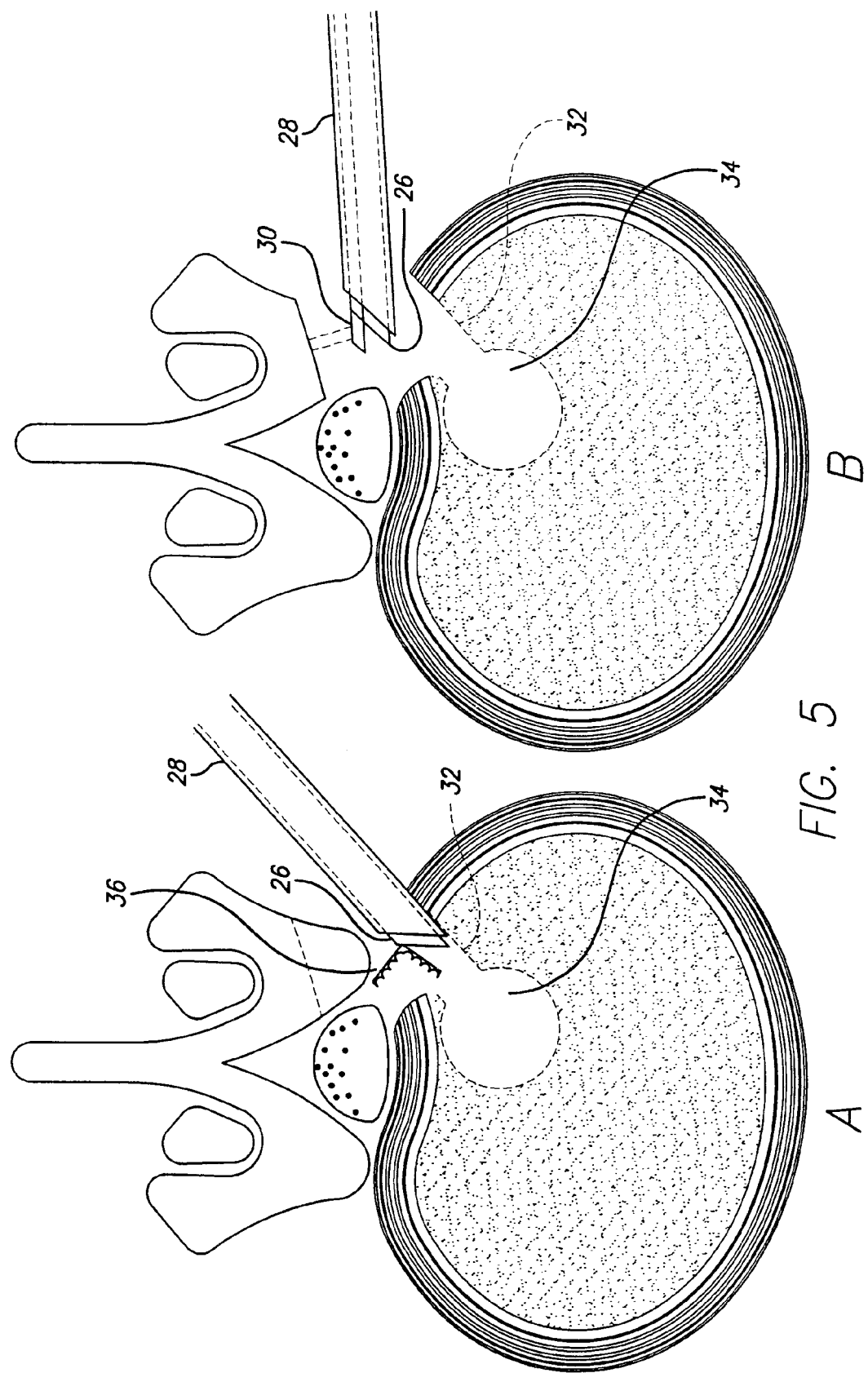
FIG. 5 demonstrates the preferred transforaminal endoscopic method in alleviated nerve compression in the foramen and the lateral recess.

Referring to FIG. 4, the thickness of the annulus is infiltrated with local anesthetic agent in four quadrants through the channels of the obturator 26. Next, the through and through fenestration of the annular window is achieved by advancing the bluntly tapered obturator 26. After the taper of the obturator 26 is advanced within the annulus, a beveled cannula 28 is placed over the obturator 26. The cannula 28 is advanced until its beveled tip straddles the annular opening. Then, the obturator 26 is removed.

Figure 3:
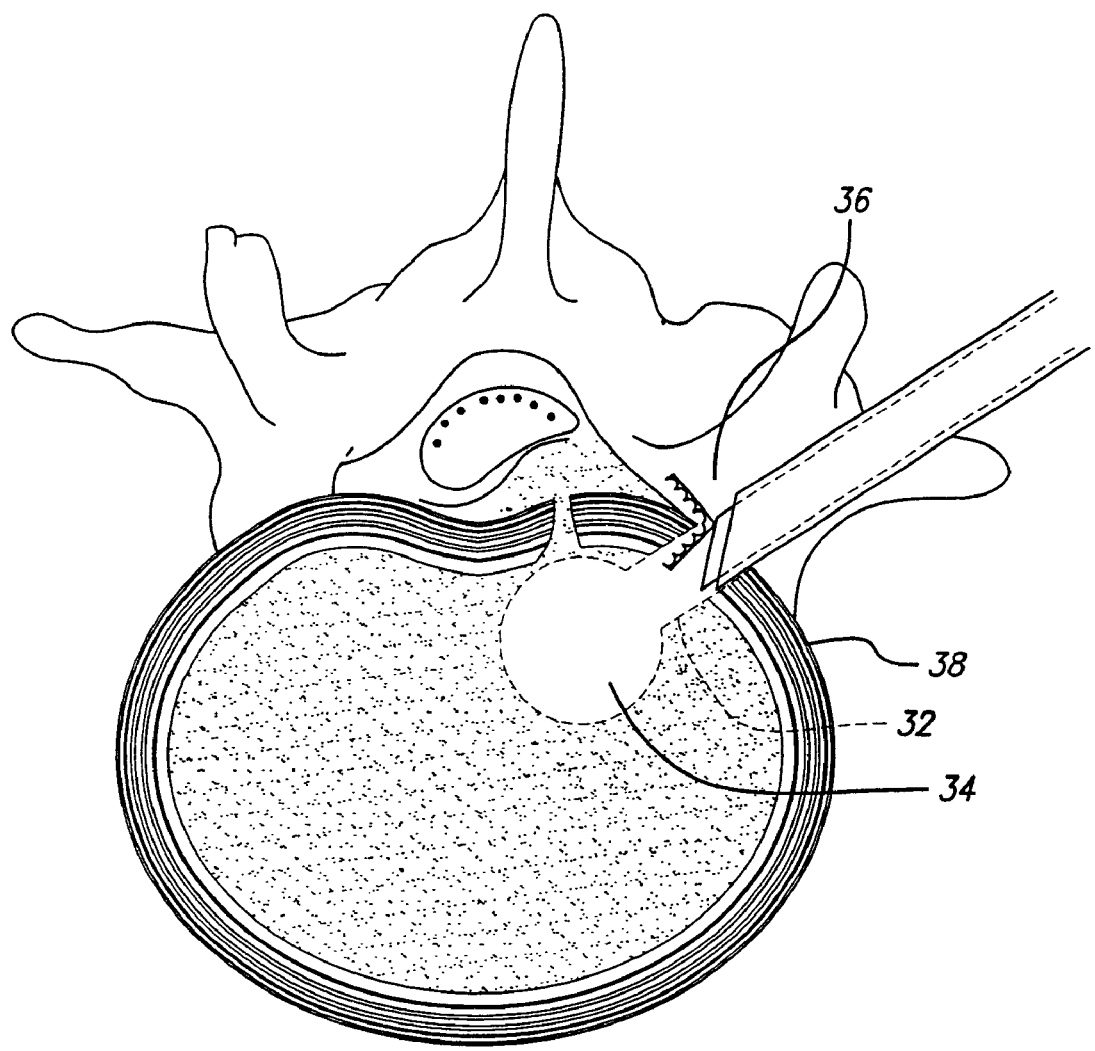
FIG. 3 presents a transforaminal endoscopic excision technique for a paramedian disc herniation.

An operating endoscope 30 is inserted into the beveled cannula 28. If the pathology is of intracanal intervertebral herniation, refer to FIG. 3 for extraction method. Referring to FIG. 3, a working soft tissue tunnel 32 and a working cavity 34 are created in the annulus. The biting forceps 36 are positioned to open the herniation annular collar 38. Once the collar is opened, the surgeon grasps the herniated nucleus fragment and pulls it out via the previously established work spaces.

Figure 9:
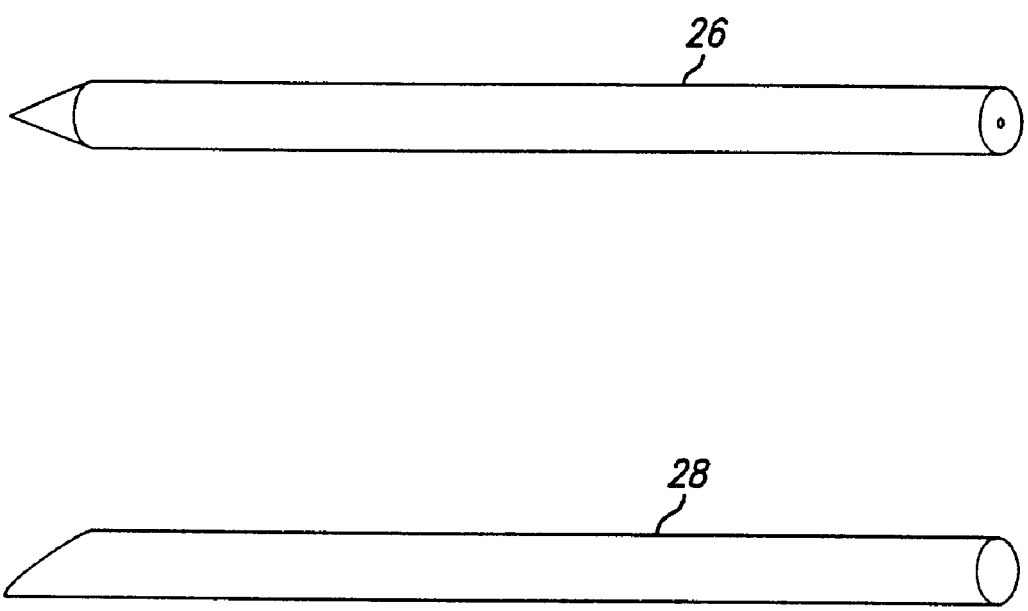
FIG. 9 presents cylindrical tools used to create a working channel from the skin window into the foraminal annular window.

If the operating pathology calls for fusion, the targeted disc space of the spine is distracted apart further using progressively larger cannulae 28 (see FIG. 9). During the disc space distraction process, the full diameter of the cannulae 28 enters the annular opening. Progressively greater distraction is achieved using sequentially larger cannulae 28. In the preferred embodiment the cannulae 28 are what are commonly known as fish mouth cannulae.

Figure 6:
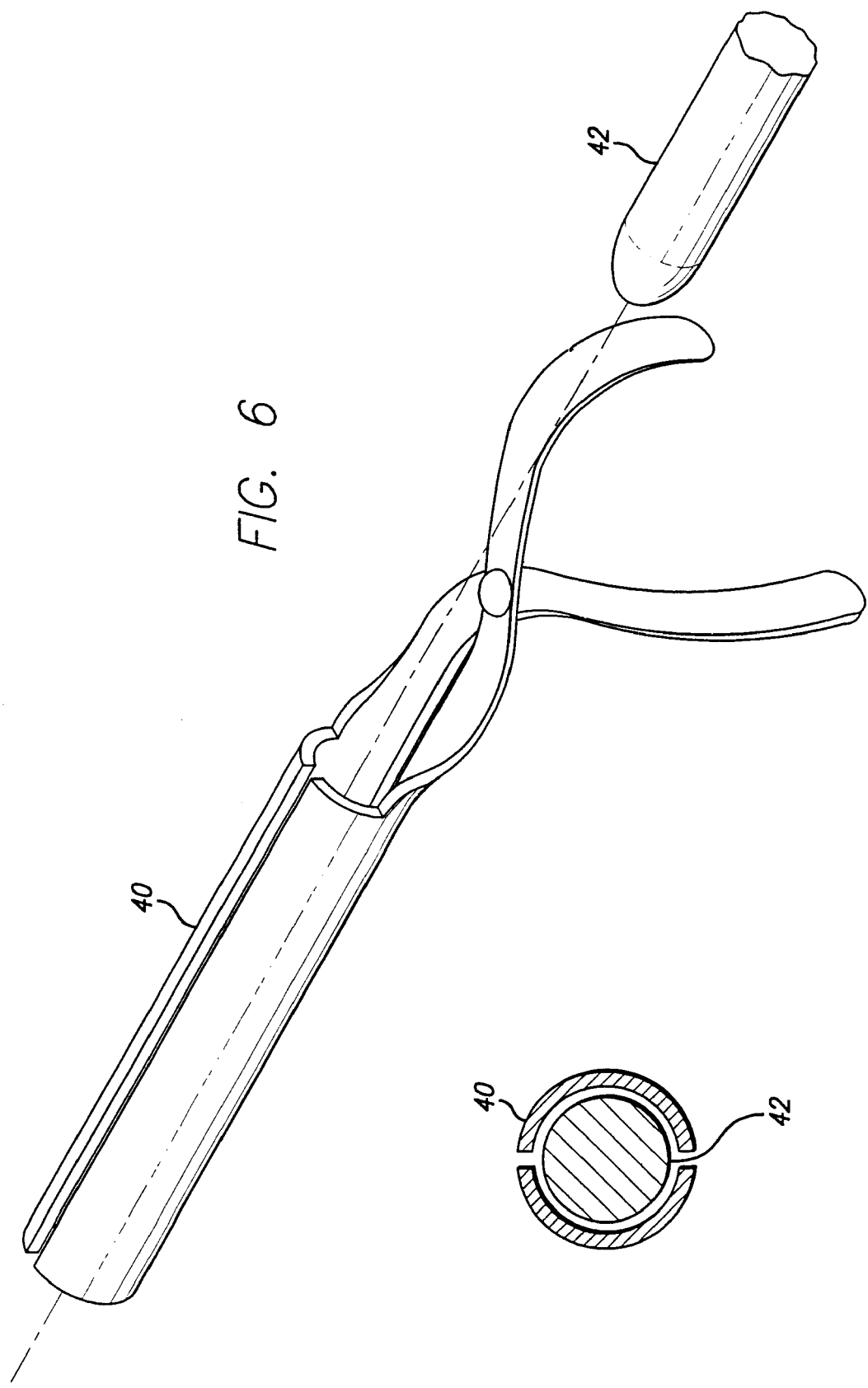
FIG. 6 presents a semi-tubular spreader, with fish mouthed end, and solid rod dilators.

When the disc space height distraction reaches anatomical maximum, a semi-tubular spreader 40 (see FIG. 6) replaces the largest sized cannula 28. The semi-tubular spreader 40 is opened further using progressively larger solid bore rods 42 until the spreader blades can achieve the desired opening. In the preferred embodiment, the opening is typically in the range of 2.5 mm–3.5 mm. The exact size necessary will be dependent on the and treatment needs of the patient. At this point, the rotational orientation of the semi-tubular spreader 40 blades is such that each blade engages the bony rims of the opposing vertebra, and the opening is substantially parallel to the disc. Up to this step, the fenestration made in the annulus remains circular in shape.

Referring next to FIGS. 3–5 and 8, once the semi-tubular spreader 40 is opened in this position, ablation of the nucleus pulposus is initially undertaken using various hand rongeurs, curettes 48, rake 46, shaver 44 and negative pressure devices. The cartilaginous end-plate and the adjacent nucleus require a more aggressive T-shaped configured debrider 42. The T-shaped debriders 42, rake and other attachments can be operated by hand or attached to a low speed, high torque power source. The softer central nucleus pulposus removal may be achieved by using a motorized shaver 44. In the surgical process for an acutely herniated disc, the motorized shaver will debride the posterior nucleus and remove unstable nucleus material from the herniation path. The annular collar may be divided by using a cutting forcep to perform a partial annulectomy in order to access extended nucleus material in the epidural space. The side walls of the annular channel may be further widened and medialized by using a Holmium-Yag laser.

In the methodology of the invention, when the disc removal has reached its desired limits and the selected amount of the nucleus pulposus and cartilagenous end plate have been removed, the excavated cavity will have roughly in the shape of a biconvex and round disc.

Figure 7:
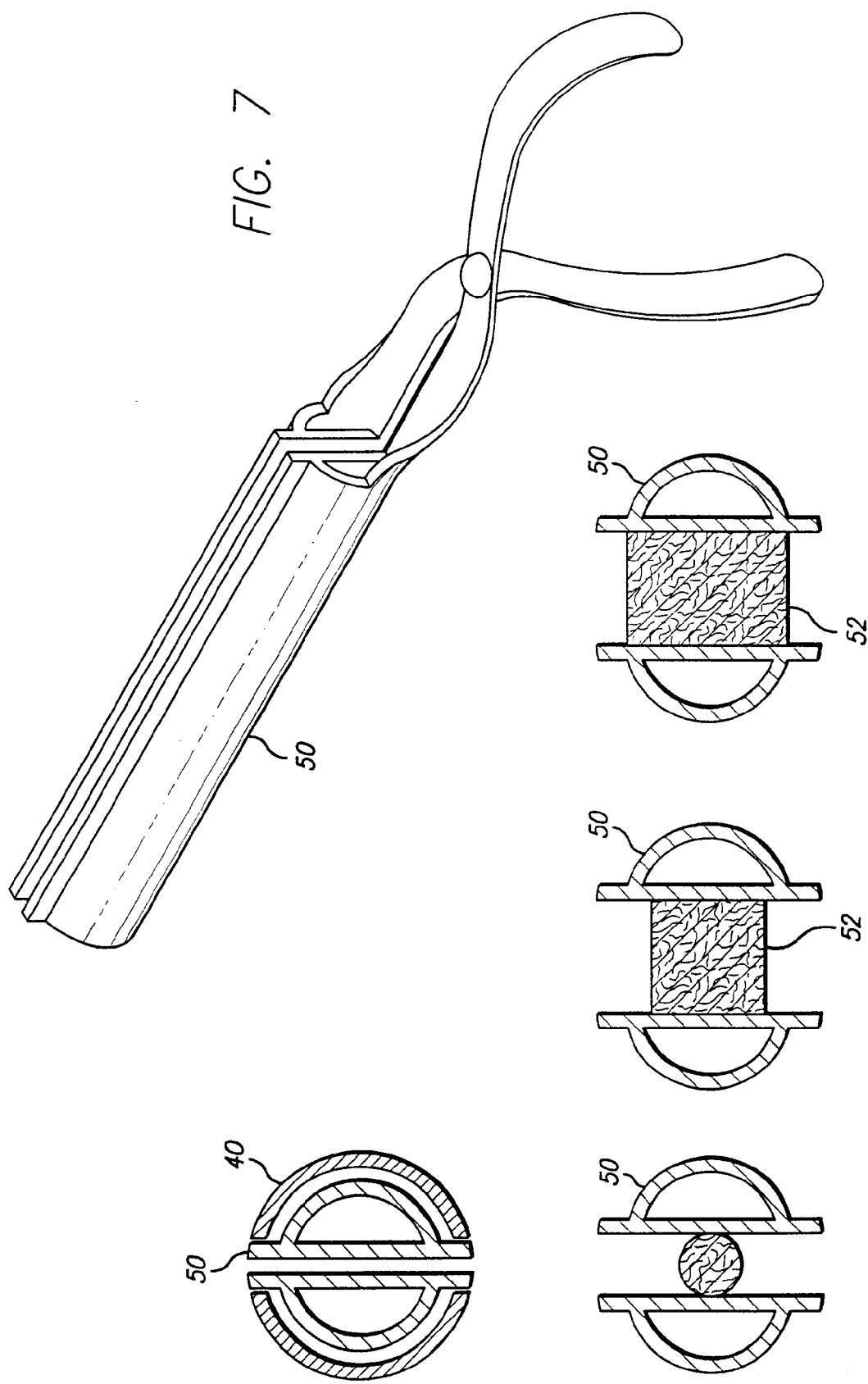
FIG. 7 presents a flat blade spreader.

The annular opening thus far is circular in its gross dimensions. Referring next to FIG. 7, the shape of the circular annular fenestration is changed, in the subsequent steps, to an angular (i.e., substantially rectangular) opening by the unique methodology of the present invention. In the preferred embodiment, the circular shaped opening is changed to a more angular opening in the shape of a square or rectangle. The angular shaped opening wastes no distracted disc space height dimension and will accept the angular graft components for maximum size and contact surfaces between the graft and the host bed.

Next, referring to FIG. 7, a flat blade spreader 50, with blades that are slightly wider than those of the semi-tubular spreader 40, is inserted into the slot of the semi-tubular spreader 40. The two embraced spreaders 40 and 50 are then rotated through an angle so that the flat blades are oriented substantially cephalad-caudad. In the preferred embodiment of the present invention, the spreaders are rotated through an angle of approximately 90 degrees. While the two spreaders are intertwined, the flat blade spreader 50 is opened moderately and the semi-tubular spreader 40 is removed. The flat blade spreader 50 is then opened to its maximum width, using a passive spreading technique. This can be achieved by using progressively thicker rectangular shaped distractor 52. The opened sides of the tunnel created by the flat blade spreader 50 are covered by attaching cover blades both on the cephadad and the caudad end of the tunnel. The covers blades are incorporated to retract soft tissue and exiting nerve away from the tunnel proper. Several cover attachment mechanisms are entertained. One is that of an attachment tunnel on the outside surface of the flat blade. Other methods of attachment mechanism include clasps and screw-ons. The enclosed tunnel makes transit of the graft components free of entanglement risks in the soft tissue.

Figure 10:
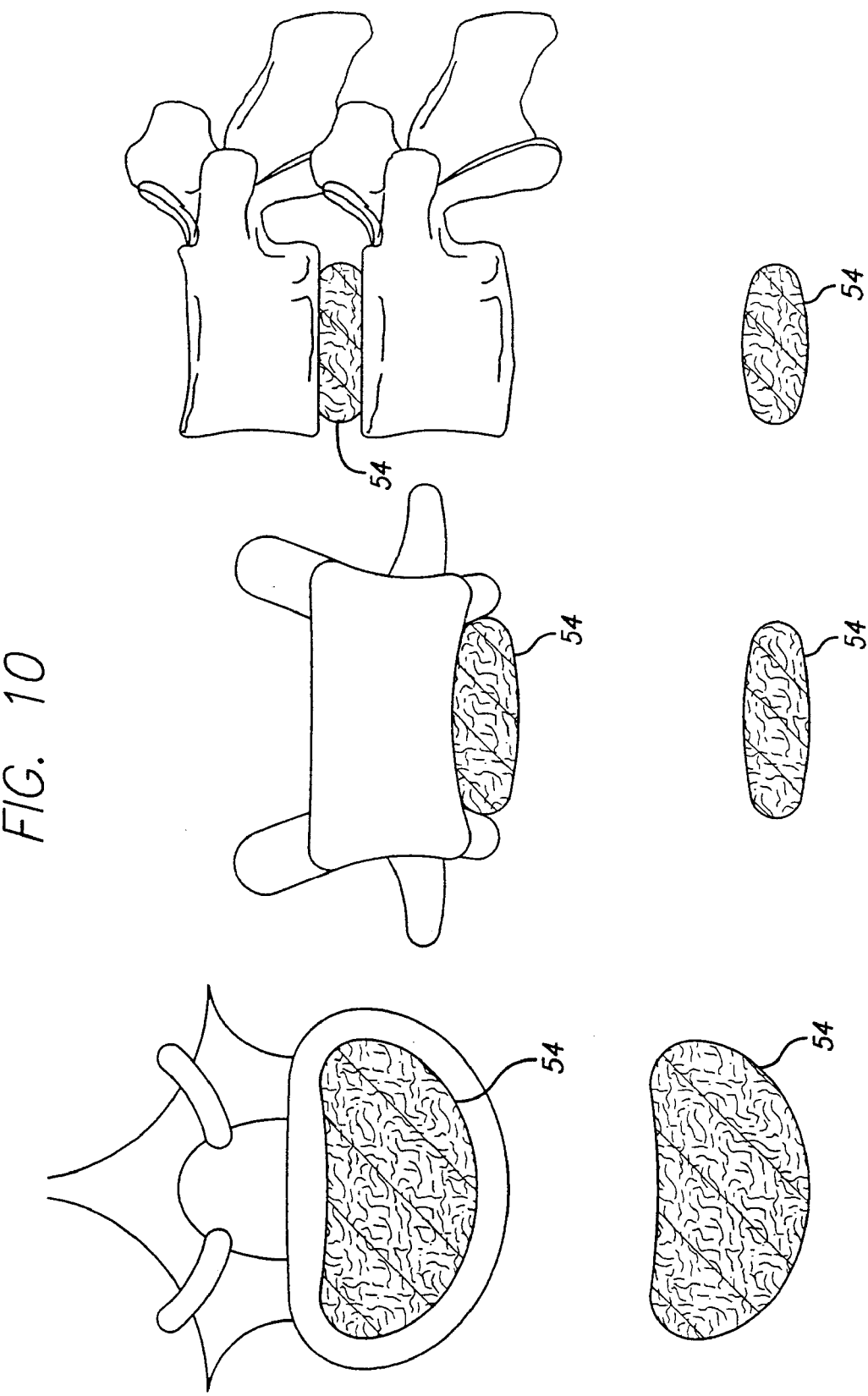
FIGS. 10 and 11 present bone graft materials used in the preferred embodiment of the present invention.

Referring next to the implant/filler material 54 shown in FIG. 10, multiple shallow perforations are made in the subchondral bone of both end-plates to allow for the entry of a blood supply for the fusion process.

Figure 11:
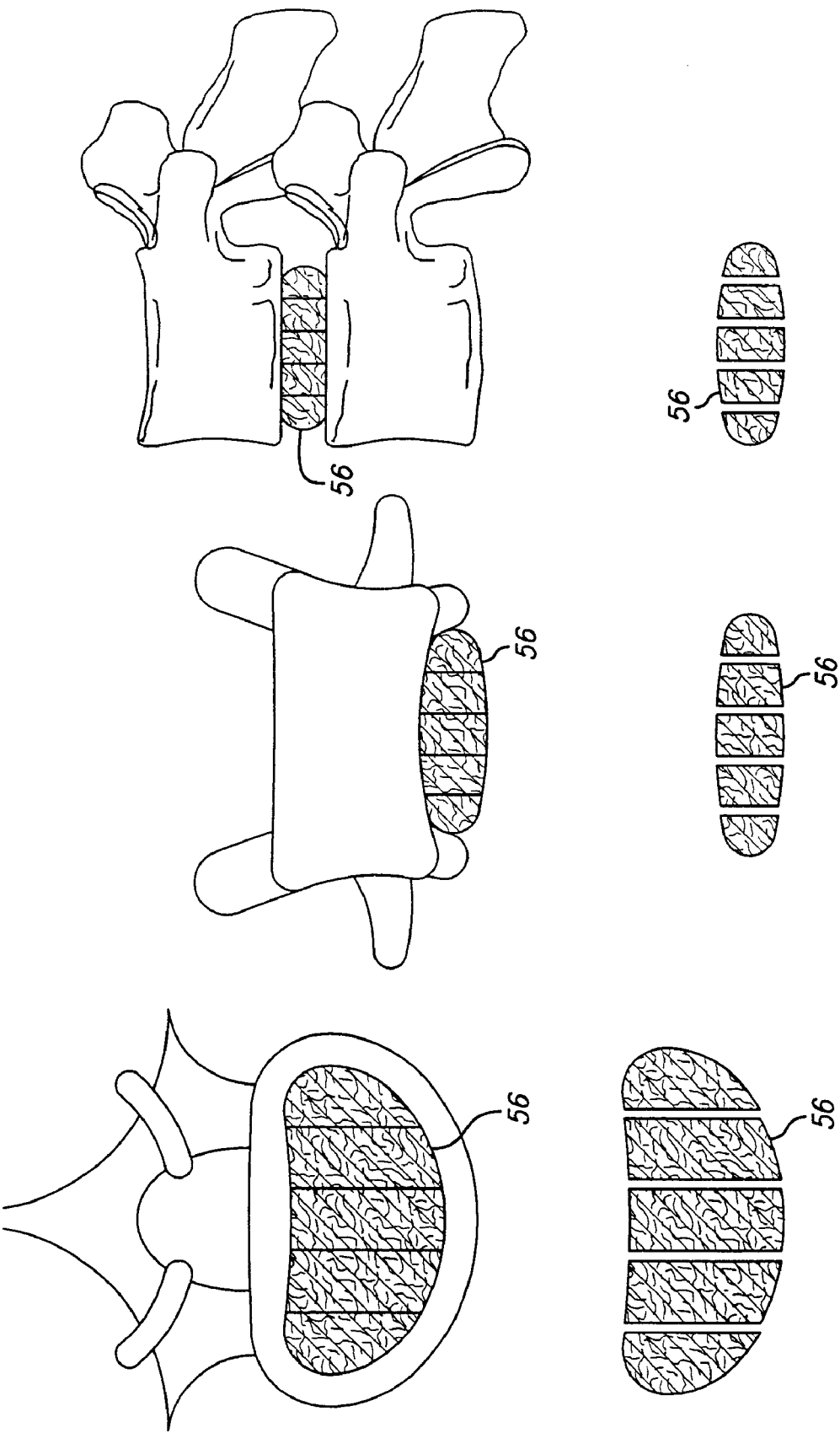

Referring next to FIG. 11, after completion of the above preparations, introduction of the optimally sized modular discoid shaped bone graft components 56 from the outside of the skin surface into the disc space is carried out. The preferred method uses at least two pieces of modular discoid graft components 56. The first piece is inserted and pushed as anteriorly as possible against the interior of the anterior annulus. Gradual seating of the graft is made possible by using various contoured impactors. Once the first graft clears the tips of the flat blade spreader 50 (see FIG. 7), the second graft is inserted. For disc space of large size, a third graft component, rectangular in shape can be introduced between the first two graft components.

The graft to be inserted should have the largest possible surface area and height to take advantage of the maximum possible contact area with the opposing host end-plates. The bone graft material should be tall enough so that the graft end-plate surfaces are under compression. The ideal vertebral interbody graft shape is that of a disc. Since the tunnel from the skin into the disc space is very limited in height and width, it is preferred to modularize the whole discoid shape into two or more components to facilitate the passage of the material through the relatively smaller tunnel.

After the insertion of the graft material, osteoconductive and osteoinductive supplementary agents in the form of paste, jelly or sponge can also be inserted to fill any small crevices or voids that remain in the target intervertebral disc space.

It will be apparent to those skilled in the art that the foregoing description is for illustrative purposes only, and that various changes and modifications can be made to the present invention without departing from the overall spirit and scope of the present invention. The full extent of the present invention is defined and limited only by the following claims.

What is claimed is:

1. A method of performing percutaneous transforaminal endoscopic lumbar surgery on a patient, comprising the steps of:

creating an opening in said patent's skin;

passing at least one tubular cannula through said opening so as to create a soft tissue tunnel;

placing a semi-tubular spreader over a said at least one tubular cannula inside said soft tissue tunnel;

placing a flat blade spreader into an opening formed by said semi-tubular spreader;

dilating said opening by spreading apart blades of said flat blade spreader;

inserting bone grafts through said opening and into an intervertebral space of said patient.

2. The method of claim 1, wherein said at least at least one tubular cannula has a first end, and said first end passes through said opening and stops substantially adjacent to said invertervebral space of said patient.

3. The method of claim 1, further comprising, after said step of placing said semi-tubular spreader, the step of removing said at least one cannula.

4. The method of claim 1, further comprising, after said step of dilating said opening, the step of rotating said flat blade spreader and said semi-tubular spreader in unison.

5. The method of claim 4, further comprising, after said rotating step, the step of removing said semi-tubular spreader.

6. The method of claim 4, wherein said flat blade spreader is rotated through an angle of approximately ninety degrees.

7. The method of claim 4, wherein said flat blade spreader is rotated through an angle such that blades of said flat blade spreader are oriented substantially cephalad-caudad.

8. The method of claim 1, wherein when said flat blade spreader is dilated, a cross section of said soft tissue tunnel is changed to be substantially rectangular in shape, and said intervertebral space is increased.

9. The method of claim 1 further comprising, prior to said step of inserting bone grafts, the step of debriding nucleus pulposus in said intervertebral space.

10. The method of claim 1, wherein said bone grafts are substantially rectangular in shape.

11. The method of claim 1, wherein said bone grafts have the shape of a flat disc.

12. A method of performing percutaneous transforaminal lumbar surgery in a patient, comprising the steps of:

creating a skin window in said patient's skin;

defining a foraminal window substantially adjacent to said a discal space of said patient;

inserting a needle through said skin window and guiding a tip of said needle to said foraminal annular window;

passing an obturator over a said needle so as to create a soft tissue tunnel in said patient, said soft tissue tunnel beginning at said skin window and terminating at said foraminal window;

removing said needle;

placing a first cannula over said obturator, within said soft tissue tunnel;

removing said obturator;

placing a plurality of progressively larger cannulae within said soft tissue tunnel so as to dilate said skin window and said soft tissue tunnel, each of said cannulae being removed after said next larger cannula is inserted;

inserting a semi-tubular spreader over one of said tubular cannulae, said semi-tubular spreader having a tube portion comprised of an upper arm and lower arm, said semi-tubular spreader being oriented such that an opening between said upper arm and said lower arm is substantially horizontal;

dilating said annular fenestration and vertebral separation by using circular rods of progressively increasing diameter inserted within said tube portion of said semi-tubular spreader;

debriding nucleus pulposus within said intervertebral space;

inserting a flat blade spreader into said semi-tubular spreader, said flat blade spreader having at least two blade portions, said blade portions fitting into said opening between said upper and lower arms of said semi-tubular spreader;

rotating said semi-tubular spreader and said flat blade spreader in unison;

removing said semi tubular spreader;

spreading said blade portions of said flat blade spreader so as to dilate said soft tissue tunnel and spread apart vertebrae adjacent to said intervertebral space;

inserting at least one substantially rectangular graft substantially anteriorly in said intervertebral space;

filling lattices of the block graft and void spaces of the interspace with osteoinductive agents.

13. The met hod of claim 12, wherein said skin window constitutes an annular fenestration.

14. The method of claim 12, wherein said semi-tubular spreader and said flat blade spreader are rotated through an angle of approximately ninety degrees.

15. A flat blade spreader for use in endoscopic lumbar surgery, comprising:

a first handle and a second handle joined together by at least one pivot point, each of said handles including a grip;

each handle having attached to it a flat surface blade extending outward at an angle from a planar surface of the first and second handle grips.

16. The device of claim 15 wherein said flat surface blades are grooved.

* * * * *